United States Patent

Ooms et al.

[11] Patent Number: 5,932,768
[45] Date of Patent: *Aug. 3, 1999

[54] PROCESS FOR THE PREPARATION OF 4-AMINODIPHENYLAMINE

[75] Inventors: Pieter Ooms, Krefeld; Ulrich Notheis, Dormagen; Christian Laue, Monheim, all of Germany

[73] Assignee: Bayer AG, Leverkusen, Germany

[ * ] Notice: This patent is subject to a terminal disclaimer.

[21] Appl. No.: 09/126,344

[22] Filed: Jul. 30, 1998

[30] Foreign Application Priority Data

Aug. 6, 1997 [DE] Germany ............... 197 34 055

[51] Int. Cl.$^6$ ................................................. C07C 209/30
[52] U.S. Cl. .................. 564/416; 564/415; 564/433; 564/434
[58] Field of Search .................. 564/415, 416, 564/433, 434

[56] References Cited

U.S. PATENT DOCUMENTS

| | | |
|---|---|---|
| 4,187,248 | 2/1980 | Merten et al. . |
| 4,187,249 | 2/1980 | Maender et al. . |
| 4,670,595 | 6/1987 | Podder et al. . |
| 5,117,063 | 5/1992 | Stern ................................... 564/398 |
| 5,420,354 | 5/1995 | Malz ................................... 564/423 |
| 5,574,187 | 11/1996 | Maiz et al. . |
| 5,606,111 | 2/1997 | Stern ................................... 564/398 |
| 5,739,403 | 4/1998 | Reinartz ............................. 564/423 |

FOREIGN PATENT DOCUMENTS

| | | |
|---|---|---|
| 784 049 | 1/1997 | European Pat. Off. . |
| 35 01 698 | 7/1986 | Germany . |
| 93/24450 | 12/1993 | WIPO . |

OTHER PUBLICATIONS

Ullmann's Encyclopedia of Industrial Chemistry, Antioxidants, Peter P. Klemchuk, vol. A3, pp. 91–111 (1985).
Kirk–Othmer, 4$^{th}$ Ed., vol. 3, Antiozonants, Robert P. Lattimer, et al., pp. 448–456 (1992).
Kirk–Othmer, 4$^{th}$ Ed., vol. 3, Antioxidants, Martin Dexter, pp. 424–427 (1992).

*Primary Examiner*—Gary Geist
*Assistant Examiner*—Jean F Vollano
*Attorney, Agent, or Firm*—Connolly and Hutz

[57] ABSTRACT

4-aminodiphenylamines are prepared by hydrogenating nitrosobenzene or mixtures of nitrosobenzene and nitrobenzene with hydrogen in the presence of bases containing hydroxide, oxide and/or alkoxide groups and heterogeneous catalysts in inert aprotic solvents at temperatures of from 0 to 200° C. and at pressures of from 0.1 to 150 bar.

9 Claims, No Drawings

PROCESS FOR THE PREPARATION OF 4-AMINODIPHENYLAMINE

The invention relates to a process for the preparation of 4-aminodiphenylamine (4-ADPA) by hydrogenating nitrosobenzene with hydrogen in the presence of hydrogenation catalysts and bases.

4-ADPA is an important intermediate for oxidants and stabilisers in the rubber and polymer industry (Kirk-Othmer, Encyclopedia of Chemical Technology, 4th Edition, 1992, Vol. 3, pp. 424–447 and 448–456; Ullmann's Encyclopedia of Industrial Chemistry, 5th Edition, Vol. A3, 1985, pp. 91–111).

4-aminodiphenylamine can be prepared by a number of methods. One possible route to 4-ADPA is a two-stage (intermediate 4-nitrodiphenylamine) reaction of aniline or aniline derivatives with p-nitrochlorobenzene in the presence of an acid acceptor or neutralising agent and optionally in the presence of a catalyst. The following are examples of publications which describe preparation by the latter method: DE-A35 01 698, DE-A 18 56 63, U.S. Pat. Nos. 4,670,595, 4,187,249, 468,333 and 4,187,248. It is disadvantageous in such a process that the halide ions which arise in this case lead to corrosion in reactors and apparatus and must be disposed of at considerable cost. For this reason aniline or corresponding aniline derivatives have been reacted with nitrobenzene in the presence of tetraalkylammonium hydroxides and in the presence of controlled quantities of protic materials. In this case a satisfactory quantity of 4-ADPA was obtained (see WO 95/00 324 and WO 93 24 450). According to U.S. Pat. No. 5,420,354, 4-ADPA can be obtained by reacting aniline, nitrobenzene and hydrogen in the presence of a hydrogenation catalyst, hydrogenation inhibitor and acid co-catalyst, but at rather unsatisfactory yields. U.S. Pat. No. 5,574,187 describes the possibility of obtaining 4-ADPA by reacting aniline with nitrosobenzene or phenyl hydroxylamine in the presence of acids.

However, the latter processes have the disadvantage that two different educts, which must be prepared in separate process steps immediately before, are used, and this is less economic.

It is also known that the hydrogenation of nitrosobenzene over heterogeneous catalysts principally delivers aniline and hydrazobenzene. 4-ADPA is not mentioned as a product (Chem. Ind. 1994, Catalysis of Organic Reactions, pp. 137–149).

It has now surprisingly been found that industrially usable yields of 4-ADPA can be obtained by hydrogenating nitrosobenzene in the presence of bases and heterogeneous catalysts.

The present invention therefore provides a process for the preparation of 4-aminodiphenylamine, which is characterised in that nitrosobenzene or mixtures of nitrosobenzene and nitrobenzene are hydrogenated with hydrogen in the presence of bases containing hydroxide, oxide and/or alkoxide groups and heterogeneous catalysts, in the presence of inert aprotic solvents at temperatures of from 0 to 200° C. and at pressures of from 0.1 to 150 bar.

Inorganic bases such as alkali metal hydroxides, alkali metal oxides, alkali metal alkoxides, alkaline earth metal hydroxides, alkaline earth metal oxides, alkaline earth metal alkoxides and the corresponding hydroxides, oxides and alkoxides of elements 58 to 71 of the Periodic Table of Elements (new IUPAC notation) are considered as bases containing hydroxide, oxide and/or alkoxide groups, which are suitable for the process according to the invention. The following are named as examples: the oxides, hydroxides and alkoxides of sodium, potassium, lithium, caesium, magnesium, calcium, barium, lanthanum and/or cerium, in particular the oxides, hydroxides and alkoxides of lithium, sodium, potassium, caesium, most particularly preferably potassium hydroxide, caesium hydroxide, sodium butylate, sodium methylate, sodium ethylate, potassium butylate, potassium methylate, potassium propylate, potassium ethylate, potassium pentylate.

Organic bases such as, for example, quaternary alkylammonium hydroxides ($NR_4^+OH^-$ having each R standing independently for alkyl, aryl or aralkyl having 1 to 7 carbon atoms) are furthermore considered. Examples which might be named are: tetramethylammonium hydroxide, tetraethylammonium hydroxide, tetrapropylammonium hydroxide, tetrabutylammonium hydroxide, methyltributylammonium hydroxide, methyltripropylammonium hydroxide, methyltriethylammonium hydroxide, trimethylbenzylammonium hydroxide. Tetramethylammonium hydroxide, tetraethylammonium hydroxide, tetrapropylammonium hydroxide and tetrabutylammonium hydroxide are particularly preferred. Tetramethylammonium hydroxide is most particularly preferably used.

Any mixtures of the aforementioned bases may also be used.

It is furthermore possible to use the inorganic bases in conjunction with phase transfer catalysts. Suitable phase transfer catalysts are described, for example, in W. E. Keller, Fluka-Kompendium, Vol. 1, 2, 3, Georg Thieme Verlag, Stuttgart 1986, 1987, 1992. For example, the bases previously mentioned may be used together with crown ether, such as 18-crown 6, or quaternary ammonium compounds.

The bases to be used according to the invention may contain up to 6 mol water, preferably up to 3 mol water, particularly preferably up to 2.5 mol water, in relation to one mole base.

The bases according to the invention may be added to the reaction mixture in solid form, as a melt or as a solution in an aprotic solvent or in a mixture of nitrosobenzene and one or more aprotic solvents.

The bases are used here in a quantity of from 0.01 to 3, preferably 0.1 to 2, in particular 0.3 to 1.5, equivalents per mole nitrosobenzene.

Aromatic hydrocarbons having 6 to 20 carbon atoms, straight-chain or cyclic ethers having up to 5 oxygen atoms and 2 to 16 carbon atoms, aromatic halogenated hydrocarbons having 6 to 20 carbon atoms and amides having 1 to 10 carbon atoms are considered as inert aprotic solvents. The solvents mentioned may naturally be used intermixed with one another. The following are in particular named as suitable solvents: benzene, toluene, xylene, tert-butyl methyl ether, tert-amyl methyl ether, diisopropyl ether, diethylene glycol dimethyl ether, glycol dimethyl ether, dioxane, tetrahydrofuran, diamyl ether, chlorobenzene, dichlorobenzene, dimethylformamide, dimethylacetamide and N-methyl pyrrolidinone. Toluene, xylene, glycol dimethyl ether, dioxane, tert-butyl methyl ether, diisopropyl ether, diethylene glycol dimethyl ether are preferably used, in particular glycol, dimethyl ether, dioxane, tert-butyl methyl ether, diethylene glycol dimethyl ether and toluene. The quantity of solvent is not critical for the process according to the invention and is dependent in particular on the reaction temperature and the type and quantity of the bases and catalysts used. The solvents are normally used in quantities of from 1 to 99 wt. %, preferably 5 to 95 wt. %, particularly preferably 15 to 90 wt. %, in relation to the total quantity of reaction mixture.

Virtually all heterogeneous catalysts which are known for hydrogenation reactions are suitable as heterogeneous catalysts for the process according to the invention. The catalysts according to the invention include metals of the groups 8 to 10 of the Periodic Table (new IUPAC notation) or copper and/or chromium on a suitable support having a metal content of from 0.01 to 50 wt. %, preferably 0.1 to 10 wt. %, in relation to the total weight of the catalyst. According to the invention, catalysts which contain one or more of the aforementioned metals may be used. The percentages by weight indicated apply to the sum of the individual percentages if a plurality of elements is present. Preferred metals are in particular platinum, palladium, rhodium and ruthenium, with platinum, palladium and rhodium being particularly preferred. Further preferred catalysts are Raney nickel and supported nickel catalysts.

According to the invention the above-mentioned metals or compounds thereof may also be used in pure form as a solid. Palladium black and platinum black may be named as examples of a metal in pure form.

The catalysts according to the invention may be prepared by a wide variety of methods which are known to those skilled in the art. For instance, solutions of one or more of the named metal compounds may be applied to the catalyst support to be used according to the invention, for example by soaking, adsorption, dipping, spraying, impregnation and ion exchange. Further elements may be added to the catalyst in known manner. It is furthermore possible to fix one or more of the named metals on the support by precipitation with a base. Alkaline (earth) metal hydroxides, for example, are considered as the base. One or more metals may be applied to the support both sequentially in any order and also simultaneously. A specific embodiment of the invention includes the application of the metal by precipitating a metal halide or a metal halide complex compound with a suitable base, and reducing the metal compound to the metal. If the supports are prepared by means of a sol-gel process, in one embodiment solutions of one or more of the named metal compounds may be added actually to the sol in a manner known to those skilled in the art.

All industrially conventional catalyst supports based on carbon, element oxides, element carbides or element salts in various forms for use are suitable materials for use according to the invention as a catalyst support. Examples of carbonaceous supports are coke, graphite, carbon black or activated carbons. Examples of element oxide catalyst supports are $SiO_2$ (natural or synthetic silica, quartz), $Al_2O_3$ ($\alpha$-, $\gamma$-$Al_2O_3$), aluminas, natural and synthetic aluminosilicates (zeolites), sheet silicates such as bentonite and montmorillonite, $TiO_2$ (rutile, anatase), $ZrO_2$, MgO or ZnO. Examples of element carbides and element salts are SiC, $AlPO_4$, $BaSO_4$, $CaCO_3$. Both synthetic materials and also supports from natural sources such as, for example, pumice, kaolin, bleaching earths, bauxites, bentonites, diatomaceous earth, asbestos or zeolites, may in principle be used.

Further useful supports for the catalysts which are usable according to the invention are element mixed oxides and hydrated oxides of elements in Groups 2 to 16 of the Periodic Table and of the rare-earth metals (atomic numbers 58 to 71), preferably of the elements Al, Si, Ti, Zr, Zn, Mg, Ca, Zn, Nb and Ce, which may be prepared, inter alia, from salts and/or alkoxides by way of mechanical mixtures, joint precipitations of salts or by way of co-gels, as is known to those skilled in the art.

Examples of mixed oxides are magnesium aluminium oxides (hydrotalcites).

The supports may be used both within the meaning of chemically uniform pure substances and also in mixture. Materials in both lump and powdered form are suitable for use according to the invention as catalyst supports. If the supported catalyst is arranged as a fixed bed, the support is preferably used as moulded bodies, for example as spheres, cylinders, rods, hollow cylinders, rings, etc. It is a matter of individual choice whether to modify catalyst supports further by extrusion, tabletting, optionally with the admixture of further catalyst supports or binders such as $SiO_2$ or $Al_2O_3$, and calcining. The internal surface of the support (BET surface) is around 1 to 2,000 $m^2/g$, preferably around 10 to 1,600 $m^2/g$, most particularly preferably around 20 to 1,500 $m^2/g$. The preparation and further processing of the catalyst supports used according to the invention are well known to those skilled in the art and constitute prior art.

Activated carbons and Si—, Al—, Mg—, Zr—and Ti—containing materials are preferably used as support materials, activated carbon and silicon—, magnesium— and aluminium—containing supports are particularly preferred.

The catalysts according to the invention may be used in batchwise process variants in quantities of from 0.01 to 20 wt. % in relation to the nitrosobenzene used, preferably in quantities of from 0.01 to 10 wt. %. If the reaction is carried out in continuous manner, for example in a stirred-tank reactor using a powdered catalyst or in the trickling phase on a fixed bed catalyst, loadings of from 0.01 to 500 g nitrosobenzene may be applied per gram of catalyst and per hour. Loadings of from 0.02 to 300 g nitrosobenzene per gram of catalyst and per hour are preferred.

Nitrosobenzene or nitrosobenzene/nitrobenzene mixtures such as arise, for example, in the preparation of nitrosobenzene from nitrobenzene, may be introduced into the process according to the invention. The nitrosobenzene content may be, for example, from 0.5 to 99%, preferably 0.5 to 98%, particularly preferably 1 to 97%.

The reaction temperatures in the process according to the invention are preferably from 0 to 200° C., in particular 25 to 150° C.; the pressures (hydrogen pressure) are around 0.1 to 150 bar, in particular 0.5 to 70 bar, most particularly preferably 1 to 50 bar.

It is possible to carry out the reaction at a constant temperature and at a constant hydrogen pressure; however, the hydrogen pressure and the temperature may also be changed during the course of the reaction or may differ in different reactors. When the process is carried out batchwise, the nitrosobenzene, the catalyst, the solvent and the base may be fed into the reactor in any order. The hydrogen supply may be terminated after a specified amount has been supplied, and optionally be continued again later.

Continuous process variants are, for example, hydrogenation in the liquid phase using a powdered suspended catalyst (slurry), hydrogenation in the trickling phase over a fixed bed catalyst or hydrogenation using a suspended catalyst in a bubble column. The reaction may be carried out in apparatus which is known to those skilled in the art for contacting solid, liquid and gaseous phases. Stirred-tank reactors, forced circulation reactors, bus reactors, bubble columns operating in co-current or counter-current flow or trickling phase reactors or cascades of the latter reactors, are in particular considered here, wherein the various reactor types may also occur concurrently in a cascade.

If the catalyst is used as a powder in the liquid phase, for mixing the reaction components the stirred tanks which are to be used are equipped with stirrers which are usable for that purpose. It is possible to use paddle stirrers, multistage impulse counter-current agitators, propeller stirrers, anchor agitators or gas dispersion stirrers.

The other substances which arise in the process according to the invention are intermediates of the hydrogenation of nitrosobenzene to aniline and can be converted without residue to aniline, which is likewise a valuable starting product for the synthesis of many industrial end products.

EXAMPLES

The Examples which follow show the way in which the reaction can be carried out at different pressures and temperatures and with the use of different catalysts, bases and solvents. The reaction products were analysed by gas chromatography (Durabond DB-5-MS; 30 m×0.25 mm ID) with n-tridecane as an internal standard, or by quantitative HPLC. Nitrosobenzene conversion in all the experiments described was complete. Working-up and sample preparation were carried out under nitrogen. The hydrogenation pressures indicated for the autoclave were readjusted manually when the pressure dropped as a result of the reaction.

The bases and catalysts used are commercial products or were prepared as described hereinbelow.

The tetramethylammonium hydroxide hydrates ($TMAOH.xH_2O$) were prepared by removing the water from a conventional commercial pentahydrate (from Aldrich) or a 25% aqueous solution (from Aldrich) at 80° C. under a vacuum generated by water jet and then by pump, or in a desiccator over phosphorus pentoxide. The water content which remained was determined by acid titration. The water content of the material used in each case is specified in the formulations.

PREPARATION OF THE CATALYSTS A, B

Catalyst A (Pd, Rh and Pt Catalysts)

The support material was heated in a muffle furnace at 350° C. for 2 hours and transferred into a 250 ml flask. A dilute aqueous solution of $PdCl_2$, $RhCl_3$ or $H_2PtCl_6$ (prepared by diluting an aqueous $H_2PtCl_6$ solution having a 25% platinum content) was added to the support material on a rotary film evaporator. The quantity of water was selected such that it was absorbed completely by the support ("incipient wetnet"). The majority of the water was then distilled off under vacuum at 60° C., and the catalyst was dried at 120° C. at <1 mbar pressure for 16 hours and reduced in a stream of 10 vol. % hydrogen in nitrogen at 300° C. for 24 hours. The noble metal content was determined by elemental analysis.

| Ex. No. | Type | Support | BET $m^2/g$ | Support (g) | "M" | "$H_2O$" | "M %" |
|---|---|---|---|---|---|---|---|
| A1 | Pd/MgO | Aldrich | 46 | 20.0 | 1.7 | 400 | 5.1 |
| A2 | Rh/HT | Hydrotalcite Südchemie | 134 | 15.0 | 2.0 | 60 | 3.9 |
| A3 | Pt/HT | Hydrotalcite Südchemie | 93 | 23.8 | 5.0 | 90 | 3.8 |

"M"; quantity of $PdCl_2$, $RhCl_3$ or $H_2PtCl_6$ solution (25% Pt content);
"$H_2O$"; quantity of added water; (in the case of $PdCl_2$ one drop conc. HCl is added)
"M %"; noble metal content of prepared catalyst, as wt. %.

Catalyst B (Pt/Activated Carbon)

475 g activated carbon (Norit-B-Supra, from Norit) were slurried in 2,600 ml deionised water, the mixture was heated to 50° C., and a solution of 87.5 g sodium formate in 400 ml deionised water was added. A mixture of 100 g of an $H_2PtCl_4$ solution (25 wt. % Pt) and 400 ml deionised water was added dropwise in 30 minutes, and stirring was carried out for one hour at 50° C. after the addition. The catalyst was then filtered under suction, washed and dried under vacuum at 60° C.

EXAMPLES 1 to 22 (Hydrogenations Under Normal Pressure)

Example 1

65 ml diethylene glycol dimethyl ether, 7.03 g (0.055 mol) $TMAOH.2.0 H_2O$ and 0.5 g of a powdered 5% Pd/C catalyst 3230 from Engelhard were placed in a 250 ml flat-ground jar purged with nitrogen and equipped with a gas dispersion stirrer, and were heated to 80° C. After this temperature was reached, the nitrogen was replaced at normal pressure with a 25 liter/hour hydrogen stream, and 5.89 g (0.055 mol) nitrosobenzene in 10 ml diethylene glycol dimethyl ether was added concurrently. After 120 minutes a sample was taken and was filtered, neutralised with ethanoic acid and analysed by quantitative gas chromatography. Nitrosobenzene conversion was complete. The 4-ADPA yield was 46.0% (percentages are mol. % in relation to nitrosobenzene).

Example 2

Example 1 was repeated with 0.5 g of a powdered 5% Pt/C catalyst (catalyst B) at 80° C. After a reaction time of 2 hours the 4-ADPA yield was 48.0%.

Example 3

The Example was repeated with 0.5 g of a powdered 5% Rh/C catalyst G 10 from Degussa at 80° C. After a reaction time of 2 hours the 4-ADPA yield was 47.0%.

Example 4

Example 1 was repeated with 0.5 g of a powdered 5% $Pt/Al_2O_3$ catalyst from Aldrich at 80° C. After a reaction time of 2 hours the 4-ADPA yield was 35.3%.

Example 5

Example 1 was repeated with 2.5 g of a powdered 1% Pt/ZSM 5 catalyst at 80° C. After a reaction time of 2 hours the 4-ADPA yield was 31.9%.

Example 6

Example 1 was repeated with 2.5 g of a powdered 1% Pt/zeolite L catalyst at 80° C. After a reaction time of 6 hours the 4-ADPA yield was 36.9%.

Example 7

Example 1 was repeated with the same catalyst at 40° C. After a reaction time of 6 hours the 4-ADPA yield was 47.9%.

Example 8

Example 1 was repeated with the same catalyst with the addition of 0.99 g (0.055 mol) water at 80° C. After a reaction time of 1 hour the 4-ADPA yield was 32.6%.

Example 9

Example 1 was repeated with the same catalyst in 75 ml toluene as the solvent at 80° C. After a reaction time of 6 hours the 4-ADPA yield was 17.3%.

Example 10

Example 1 was repeated with the same catalyst at 25° C. After a reaction time of 14 hours the 4-ADPA yield was 26.1%.

Example 11

Example 1 was repeated with 0.5 g of a powdered 5% Pd/MgO catalyst (catalyst A1) at 80° C. After a reaction time of 6 hours the 4-ADPA yield was 14.4%.

Example 12

Example 1 was repeated with 3.1 g (0.055 mol) KOH at 80° C. After a reaction time of 1.5 hours the 4-ADPA yield was 3.9%.

Example 13

Example 1 was repeated with 6.2 g (0.055 mol) KOt-$C_4H_9$ at 80° C. After a reaction time of 10 hours the 4-ADPA yield was 3.1%.

Example 14

Example 1 was repeated with 6.2 g (0.055 mol) KOt-$C_4H_9$ and 8.5 g (0.055 mol) $(H_3C)_4NBr$ at 80° C. After a reaction time of 18 hours the 4-ADPA yield was 9.4%.

Example 15

Example 1 was repeated with 2.5 g (0.055 mol) NaOH at 80° C. After a reaction time of 1 hour the 4-ADPA yield was 1.0%.

Example 16

Example 1 was repeated with 0.5 g of a powdered 3.9 % Rh/hydrotalcite catalyst (catalyst A2) at 80° C. After a reaction time of 2 hours the 4-ADPA yield was 22.0%.

Example 17

Example 1 was repeated with 0.5 g of a powdered 3.8% Pt/hydrotalcite catalyst (catalyst A3). After a reaction time of 2 hours the 4-ADPA yield was 28.3%.

Example 18 (Comparative Example)

Example 1 was repeated with the same catalyst without the addition of base at 80° C. After a reaction time of 14 hours the 4-ADPA yield was <0.3%.

Example 19

Example 1 was repeated with a mixture of 1.18 g (0.011 mol) nitrosobenzene and 5.42 g (0.044 mol) nitrobenzene at 80° C. After a reaction time of 1 hour the 4-ADPA yield was 60.8%.

Example 20

Example 1 was repeated with a mixture of 2.95 g (0.0275 mol) nitrosobenzene and 3.39 g (0.0275 mol) nitrobenzene at 80° C. After a reaction time of 1 hour the 4-ADPA yield was 35.2%.

Example 21 (Reaction Under Pressure)

133 g of TMAOH.2.3 $H_2O$, 960 ml diethylene glycol dimethyl ether (Diglyme) and 2.4 g of a 5% Pt/C catalyst (catalyst B) were heated to 70° C. in a 2 liter Büchi glass autoclave with a fourfold propeller stirrer. The autoclave was rendered inert with nitrogen, and 107.1 g nitrosobenzene were added. Hydrogenation was then performed for 4.4 hours at 80° C., at 4 bar hydrogen and a stirring speed of 1000 rpm.

After the reaction had ended the pressure in the autoclave was released, the autoclave was purged with nitrogen, and 500 ml deionised water were added at 50° C. Two phases formed. The mixture was filtered, and the phases were separated. The organic phase was extracted by shaking four times with 300 ml deionised water and was then neutral. The aqueous phase was extracted by shaking three times with 400 ml toluene and 50 g NaCl.

The organic phases were analysed by quantitative HPLC and were found to contain 48.4 g 4-ADPA (53.0% in relation to nitrosobenzene).

We claim:

1. A process for the preparation of 4-aminodiphenylamine, the process comprising hydrogenating nitrosobenzene or mixtures of nitrosobenzene and nitrobenzene with hydrogen in a reaction mixture consisting essentially of at least one base containing hydroxide, oxide and/or alkoxide groups and a heterogeneous catalyst, in the presence of inert aprotic solvent at temperatures of from 0 to 200° C. and at pressures of from 0.1 to 150 bar.

2. A process according to claim 1, wherein hydrogenation is performed at temperatures of from 25 to 150° C. and at pressures of from 0.5 to 70 bar.

3. A process according to claim 1, wherein the bases containing hydroxide, oxide and/or alkoxide groups are selected from the group consisting of alkali metal hydroxides, alkali metal oxides, alkaline earth metal hydroxides, alkaline earth metal oxides, alkali metal alkoxides, alkaline earth metal alkoxides and the corresponding hydroxides, alkoxides and oxides of elements 58 to 71 of the Periodic Table of Elements and quaternary alkylammonium hydroxides.

4. A process according to claim 1, wherein the base is used in quantities of from 0.01 to 3 equivalents per mole nitrosobenzene.

5. A process according to claim 1, wherein the aprotic solvent is selected from aromatic hydrocarbons having 60 to 20 carbon atoms, straight-chain or cyclic ethers having up to 5 oxygen atoms and 2 to 16 carbon atoms, aromatic halogenated hydrocarbons having 6 to 20 carbon atoms and amides having 1 to 10 carbon atom.

6. A process according to claim 1, wherein the inert aprotic solvent is used in quantities of from 1 to 99 wt. % in relation to the total quantity of reaction mixture.

7. A process according to claim 1, wherein metals of Groups 8 to 10 of the Periodic Table (new IUPAC notation) or copper and/or chromium, optionally applied to a catalyst support, are used as heterogeneous catalysts.

8. A process according to claim 1, wherein the catalyst is used in a batchwise operation in quantities of from 0.01 to 20 wt. % in relation to nitrobenzene.

9. A process according to claim 1, wherein the catalyst is used in a continuous operation with loadings of from 0.01 to 500 g nitrosobenzene are applied per gram of catalyst and per hours.

* * * * *